United States Patent
Sunagawa

(10) Patent No.: US 10,960,118 B2
(45) Date of Patent: Mar. 30, 2021

(54) SYSTEMS AND METHODS FOR CONTROLLING A HEART PUMP TO MINIMIZE MYOCARDIAL OXYGEN CONSUMPTION

(71) Applicant: ABIOMED, INC., Danvers, MA (US)

(72) Inventor: Kenji Sunagawa, Fukuoka (JP)

(73) Assignee: ABIOMED, INC., Danvers, MA (US)

( * ) Notice: Subject to any disclaimer, the term of this patent is extended or adjusted under 35 U.S.C. 154(b) by 33 days.

(21) Appl. No.: 16/050,542

(22) Filed: Jul. 31, 2018

(65) Prior Publication Data
US 2020/0038569 A1 Feb. 6, 2020

(51) Int. Cl.
| | | |
|---|---|---|
| *A61M 1/12* | (2006.01) | |
| *A61B 5/02* | (2006.01) | |
| *A61M 1/10* | (2006.01) | |
| *A61N 1/365* | (2006.01) | |

(52) U.S. Cl.
CPC ......... *A61M 1/122* (2014.02); *A61B 5/02028* (2013.01); *A61M 1/1086* (2013.01); *A61N 1/36571* (2013.01)

(58) Field of Classification Search
CPC .................................................. A61M 1/1086
See application file for complete search history.

(56) References Cited

U.S. PATENT DOCUMENTS

| | | | |
|---|---|---|---|
| 3,677,092 A | 7/1972 | Guarino | |
| 3,911,897 A * | 10/1975 | Leachman, Jr. ...... | A61M 1/122 600/17 |
| 4,598,579 A | 7/1986 | Cummings et al. | |
| 5,437,284 A | 8/1995 | Trimble | |

(Continued)

FOREIGN PATENT DOCUMENTS

| | | |
|---|---|---|
| EP | 2 298 375 A1 | 3/2011 |
| WO | 97/49439 | 12/1997 |

(Continued)

OTHER PUBLICATIONS

International Search Report for PCT/EP2017/070953, dated Nov. 20, 2017 (3 pages).
International Search Report for PCT/EP2017/076295, dated Jan. 15, 2018 (6 pages).
International Search Report for PCT/US2018/036757, dated Sep. 10, 2018 (5 pages).

(Continued)

*Primary Examiner* — George R Evanisko
(74) *Attorney, Agent, or Firm* — Botos Churchill IP Law LLP

(57) ABSTRACT

Various systems, devices, and methods are disclosed herein for treating acute myocardial infarction (AMI) patients using a heart pump controlled in a manner that maximizes mechanical unloading of the left ventricle in the presence of cardiovascular instability and minimizes myocardial oxygen consumption (MVO2) and consequentially infarct size to prevent the development of subsequent heart failure. In a closed feedback system, the system can include a sensor configured to generate an output used to measure or calculate a left ventricular systolic pressure (LSVP) within the left ventricle of a heart and a controller coupled to a heart pump. The controller can be configured to measure or calculate the LVSP based on the output of the sensor and to control an operation of the heart pump to maximize mechanical unloading of the left ventricle based on the measured or calculated LVSP.

20 Claims, 9 Drawing Sheets

(56) References Cited

U.S. PATENT DOCUMENTS

| | | | |
|---|---|---|---|
| 6,159,160 | A | 12/2000 | Hsei et al. |
| 6,176,822 | B1 | 1/2001 | Nix et al. |
| 6,234,759 | B1 | 5/2001 | Hennel et al. |
| 6,623,420 | B2 | 9/2003 | Reich et al. |
| 7,010,954 | B2 | 3/2006 | Siess et al. |
| 7,022,100 | B1 | 4/2006 | Aboul-Hosn et al. |
| 2003/0139643 | A1 | 7/2003 | Smith et al. |
| 2004/0039243 | A1 | 2/2004 | Bearnson et al. |
| 2004/0106874 | A1 | 6/2004 | Eigler et al. |
| 2008/0097226 | A1* | 4/2008 | McConnell ............ A61B 5/024 600/485 |
| 2010/0222635 | A1* | 9/2010 | Poirier .................. A61M 1/122 600/16 |
| 2012/0095523 | A1 | 4/2012 | Yared |
| 2013/0046129 | A1 | 2/2013 | Medvedev et al. |
| 2014/0296615 | A1 | 10/2014 | Franano |
| 2015/0246166 | A1 | 9/2015 | Greatrex et al. |
| 2016/0367740 | A1 | 12/2016 | Aboul-Hosn et al. |
| 2017/0136164 | A1 | 5/2017 | Yeatts |
| 2017/0239407 | A1 | 8/2017 | Hayward |
| 2018/0146864 | A1 | 5/2018 | Jansen et al. |
| 2019/0076588 | A1* | 3/2019 | Ochsner ................ A61M 1/122 |

FOREIGN PATENT DOCUMENTS

| | | |
|---|---|---|
| WO | 98/43688 A1 | 10/1998 |
| WO | 03/015609 A2 | 2/2003 |
| WO | 03/082379 A1 | 10/2003 |
| WO | 2004/017818 | 3/2004 |
| WO | 2005/051838 A2 | 6/2005 |
| WO | 2010/099287 A1 | 9/2010 |
| WO | 2011/090927 A1 | 7/2011 |
| WO | 2014/062911 | 4/2014 |
| WO | 2014/085806 A1 | 6/2014 |
| WO | 2015/040222 A2 | 3/2015 |
| WO | 2018/036927 | 3/2018 |
| WO | 2018/073150 | 4/2018 |
| WO | 2018/146045 | 8/2018 |

OTHER PUBLICATIONS

International Search Report PCT/US2017/052259, dated Dec. 19, 2017 (3 pages).

International Search Report PCT/US2019/038039, dated Sep. 5, 2019 (5 pages).

International Search Report PCT/US2019/038049, dated Sep. 5, 2019 (5 pages).

Rüschen et al., "Online cardiac output estimation during transvalvular left ventricular assistance," Computer Methods and Programs in Biomedicine, vol. 171: 87-97 (2019).

Rüschen et al., "Robust Assistance Control of Left Ventricular Assist Devices," IFMBE Proceedings, vol. 65(13): 294-297 (2017).

Sekii et al., "Beat-to-Beat Prediction of Left Ventricular Output During Left Ventricular Bypass Pumping," Proceedings of the Annual International Conference of the IEEE Engineering in Medicine and Biology Society: 10th Annual International Conference— Nov. 4, 1988: 1773-1775.

Stolinski, et al, "The heart-pump interaction: Effects of a microaxial blood pump", International Journal of Artificial Organs, vol. 25, No. 11, pp. 1082-1088 (2002).

International Search Report PCT/US2019/044032, dated Nov. 6, 2019 (2 pages).

International Search Report and Written Opinion for Application No. PCT/US2019/044032 dated Nov. 6, 2019.

\* cited by examiner

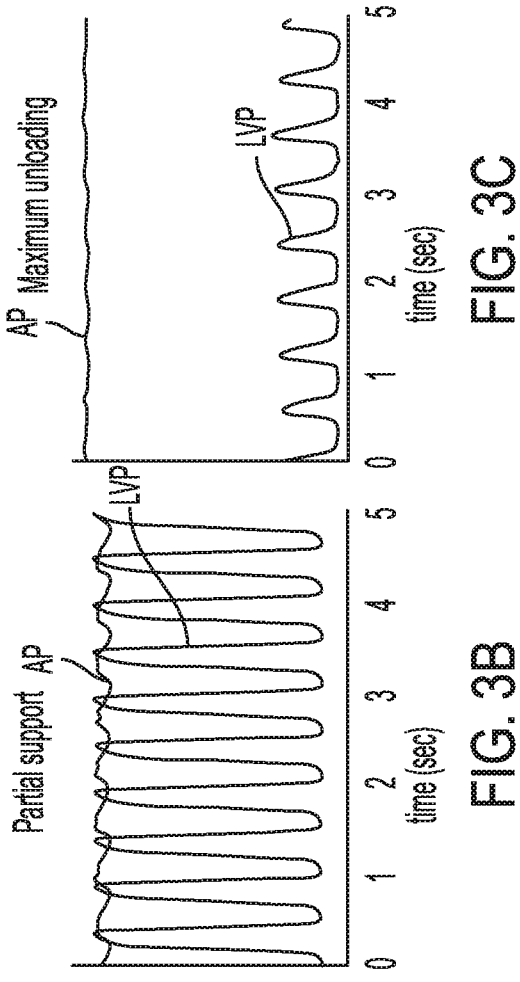
FIG. 3A
FIG. 3B
FIG. 3C
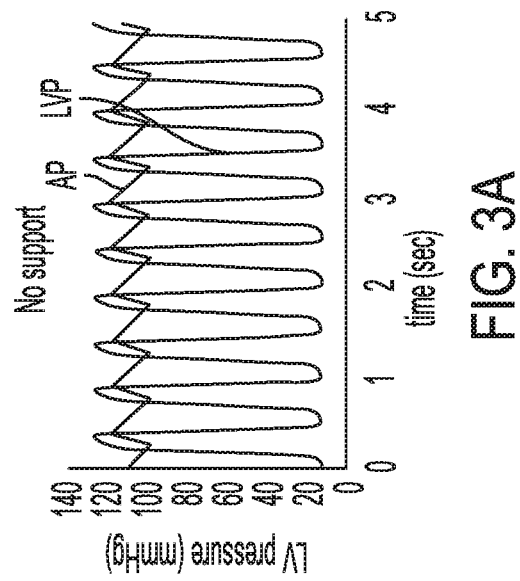
FIG. 3D
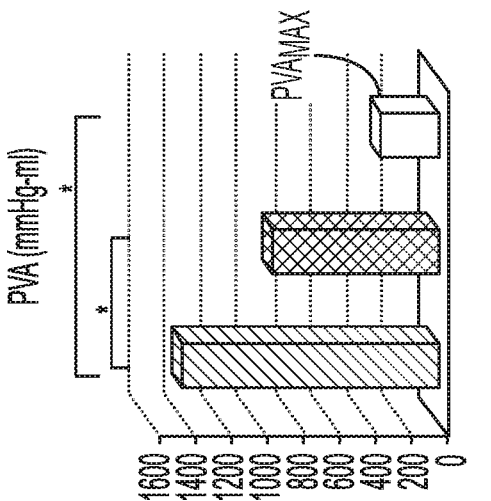
FIG. 3E
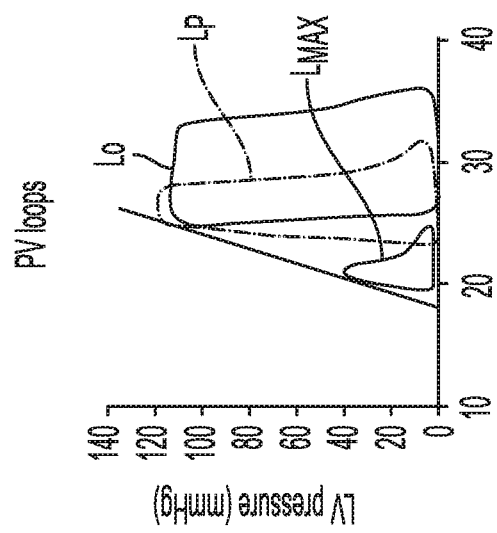
FIG. 3F

SYSTEMS AND METHODS FOR CONTROLLING A HEART PUMP TO MINIMIZE MYOCARDIAL OXYGEN CONSUMPTION

FIELD

The present disclosure relates to systems for controlling a heart pump and related methods to treat patients with acute myocardial infarction (AMI), and specifically to a closed feedback control system for controlling the operation of a heart pump to maximize mechanical unloading of the left ventricle (LV) during treatment of AMI patients and minimize myocardial oxygen consumption ($MVO_2$) and consequently infarct size to prevent the development of long term heart failure.

BACKGROUND

AMI, commonly known as a heart attack, can be a life-threatening condition that occurs when blood flow to the heart muscle is abruptly cut off, causing tissue damage. Dead tissue, or infarct, can form in the heart due to inadequate blood supply to an affected area. AMI is usually the result of a blockage in one or more of the coronary arteries. The coronary arteries carry oxygen rich blood to the heart muscle. When these arteries become blocked or narrowed, the blood flow to the heart can decrease significantly or stop completely.

AMI can require immediate medical treatment that restores blood flow through blocked arteries, sometimes referred to as reperfusion therapy. Reperfusion therapy can include surgery to remove or circumvent a blockage, such as percutaneous coronary intervention (PCI), coronary angioplasty, and bypass surgery, for example. Reperfusion therapy can alternatively or additionally include administrations of different medications, including but not limited to thrombolytics, fibrinolytics, beta-blockers, and nitroglycerin.

In some AMI patients, heart pumps can be used to stabilize hemodynamics and make it possible to perform safe and effective reperfusion therapy to salvage affected ischemic myocardium. For example, recent clinical trials as well as basic investigations demonstrated that an LV assist device (LVAD) can be used to mechanically unload the LV by withdrawing blood from the LV and infusing withdrawn blood into the aorta. Mechanical unloading can markedly reduce the work performed by the LV and thus reduce $MVO_2$. It has been observed that a reduction in $MVO_2$ can reduce infarct size, i.e., the area of dead tissue caused by a heart attack. The extent of infarct size reduction generally parallels the reduction in $MVO_2$.

Despite such a beneficial impact of mechanical unloading of the LV on AMI, its clinical applications have yet to be established. In patients with chronic heart failure, manual control of LVAD flow rate (e.g., liters per minute) can achieve stable hemodynamics. In AMI patients, however, cardiac and hemodynamic conditions are inherently unstable because AMI can drastically change cardiac contractility, vascular resistance, blood pressure, stressed volume, heart rate and/or the activity of sympathetic and parasympathetic autonomic nervous systems in seconds, minutes, or hours. These variabilities are known to strikingly influence hemodynamics. Therapeutic interventions, such as drug therapy and reperfusion, can further induce complex dynamic modulation on those variables and results in complicated hemodynamics.

In the presence of such cardiovascular instability in AMI, it can be difficult, if not impractical, to avoid mechanical unloading the LV too much or too little even with constant monitoring or continuous manual precise adjustment of the LVAD flow rate. Mechanical unloading of the LV at a flow rate a little higher than the filling rate coming from the pulmonary venous system can cumulatively reduce LV volume and eventually induce suction that can collapse the heart, trigger life-threatening arrhythmias and seriously injure myocardium. Conversely, mechanical unloading of the LV at a flow rate a little less than the filling rate increases LV volume and $MVO_2$, and thereby makes it difficult to reduce infarct size of the LV. Therefore, manual control of a heart pump to optimally unload the LV is impractical, ineffective, and potentially life threatening.

Accordingly, there is a need for improved systems and related methods for treating AMI patients using a heart pump controlled in a manner that optimizes mechanical unloading of the LV regardless of the presence of cardiovascular instability, and thereby optimally reduces $MVO_2$ and infarct size.

SUMMARY

The present disclosure is directed to various systems, devices, and methods for treating AMI patients using a heart pump controlled in a manner that maximizes mechanical unloading of the LV in the presence of cardiovascular instability and minimizes $MVO_2$ and consequentially infarct size to prevent the development of subsequent heart failure.

In one exemplary embodiment of a system for controlling a heart pump, the system includes a sensor configured to generate an output used to measure or calculate a left ventricular systolic pressure (LSVP) within the left ventricle of a heart and a controller coupled to a heart pump and configured to measure or calculate the LVSP based on the output of the sensor and to control an operation of the heart pump to maximize mechanical unloading of the left ventricle based on the measured or calculated LVSP.

In some embodiments, the controller can be configured to control one or more of a pump speed and a flow rate of the heart pump, such that the LVSP within the left ventricle is maintained at a target reference pressure. The target reference pressure can be set to a fraction of an end-systolic pressure in a normal ejecting beat, the fraction being between about 0.2 and about 0.4. The target reference pressure can be set to a fraction of a mean aortic pressure, the fraction being between about 0.2 and about 0.4. The target reference pressure can be set to minimize a pressure-volume area (PVA) of the left ventricle. For example, in some embodiments, the target reference pressure can be set to minimize the PVA of the left ventricle by about 90% to about 97%. The target reference pressure can be set to minimize myocardial oxygen consumption ($MVO_2$) of the left ventricle. For example, in some embodiments, the target reference pressure can be set to minimize the $MVO_2$ of the left ventricle by about 45% to about 48.5%.

In some embodiments, the controller can be configured to control pump speed and/or the flow rate of the heart pump to maintain the LVSP at the target reference pressure based on a plant transfer function that models changes in LVSP in response to changes in pump speed. For example, in some embodiments, the plant transfer function can be a second order delay system with a time lag defined as:

$$H(f) = \frac{K}{1 + 2\zeta \frac{f}{f_N} j + \left(\frac{f}{f_N} j\right)^2} \exp(-2\pi f L j),$$

where K is a gain, $\zeta$ is a damping factor, $f_N$ is the natural frequency, and L is the time lag. In some embodiments, the gain K can be equal to about 0.013 mmHg/rpm, the damping factor $\zeta$ can be equal to about 1.9, the natural frequency $f_N$ can be equal to about 0.41 Hz and the time lag L can be equal to about 0.03 seconds.

In some embodiments, the controller can be configured to control the pump speed and/or the flow rate of the heart pump such that the LVSP reaches the target reference pressure in less than a clinically predetermined response time and with an overshoot less than 10% of the target reference pressure. The controller can be configured to control the pump speed and/or the flow rate of the heart pump to maintain the LVSP at the target reference pressure when an open loop gain of the plant transfer function changes by a factor of 16 or less. In some embodiments, the controller can include a proportional-integral controller configured with a proportional gain equal to about 40, an integral gain equal to about 20, and a derivative gain equal to about 0. In some embodiments, the controller can include an adaptive control mechanism configured to update the plant transfer function and reconfigure the controller to control the pump speed and/or the flow rate of the heart pump in response to changes in the plant transfer function.

In one exemplary embodiment of a method for treating an acute myocardial infarction (AMI) patient, the method includes measuring or calculating an LSVP within the LV of the heart of a patient and controlling an operation of a heart pump to maximize mechanical unloading of the LV based on the measured or calculated LVSP. The heart pump is implanted in the heart to perform mechanically unloading of blood from the LV into the aorta.

In some embodiments, controlling an operation of the heart pump can include controlling one or more of a pump speed and a flow rate of the heart pump, such that the LVSP within the left ventricle is maintained at a target reference pressure. The target reference pressure can be set to a fraction of an end-systolic pressure in a normal ejecting beat, the fraction being between about 0.2 and about 0.4. The target reference pressure can be set to a fraction of a mean aortic pressure, the fraction being between about 0.2 and about 0.4. The target reference pressure can be set to minimize a pressure-volume area (PVA) of the left ventricle by about 90% to about 97%. The target reference pressure can be set to minimize myocardial oxygen consumption (MVO$_2$) of the left ventricle by about 45% to about 48.5%.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments:

FIGS. 3A-3F illustrate the effects of mechanical unloading of the LV by a heart pump on hemodynamics, pressure-volume loops, PVA and LVSP.

DETAILED DESCRIPTION

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. In the present disclosure, like-numbered components of various embodiments generally have similar features when those components are of a similar nature and/or serve a similar purpose. A person skilled in the art, in view of the present disclosure, will understand various instances in which like-numbered components across various figures are akin.

The present disclosure is directed to various systems, devices, and methods for treating AMI patients using a heart pump controlled in a manner that maximizes mechanical unloading of the LV in the presence of cardiovascular instability and minimizes MVO$_2$ and consequentially infarct size to prevent the development of subsequent heart failure.

Figure 1A:
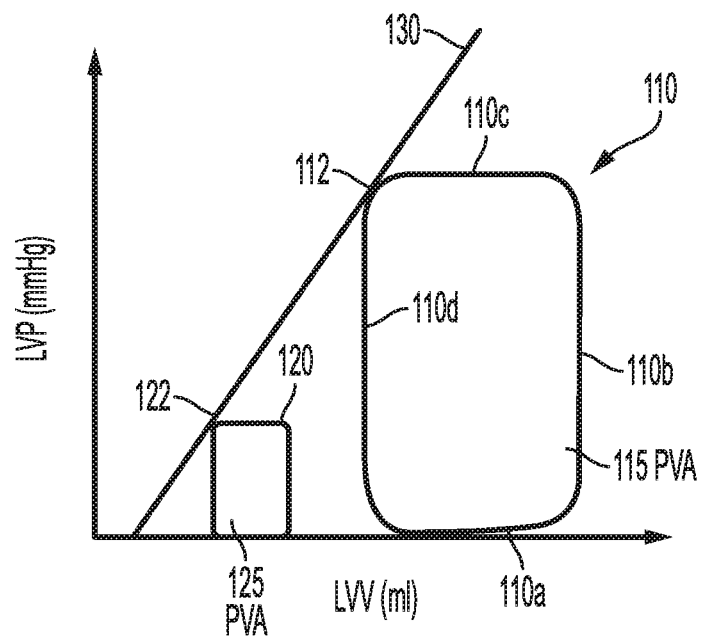
FIG. 1A illustrates the pressure-volume relationship of the LV during a cardiac cycle using exemplary pressure-volume loops.

FIG. 1A illustrates the pressure-volume relationship of the LV during a cardiac cycle. Each of the pressure-volume loops 110 and 120 represents approximate LV pressure and LV volume measurements during a complete cardiac cycle. A cardiac cycle, or heartbeat, can be divided into four basic phases: ventricular filling 110a, isovolumetric contraction 110b, systolic ejection 110c, and isovolumetric relaxation 110d. It has been well established that the end-systolic pressure is linearly correlated with end-systolic volume and has been denoted as the end-systolic pressure-volume relationship (ESVPR, line 130). ESPVR is substantially insensitive to changes in loading conditions and its slope well represents ventricular contractility.

Figure 1B:
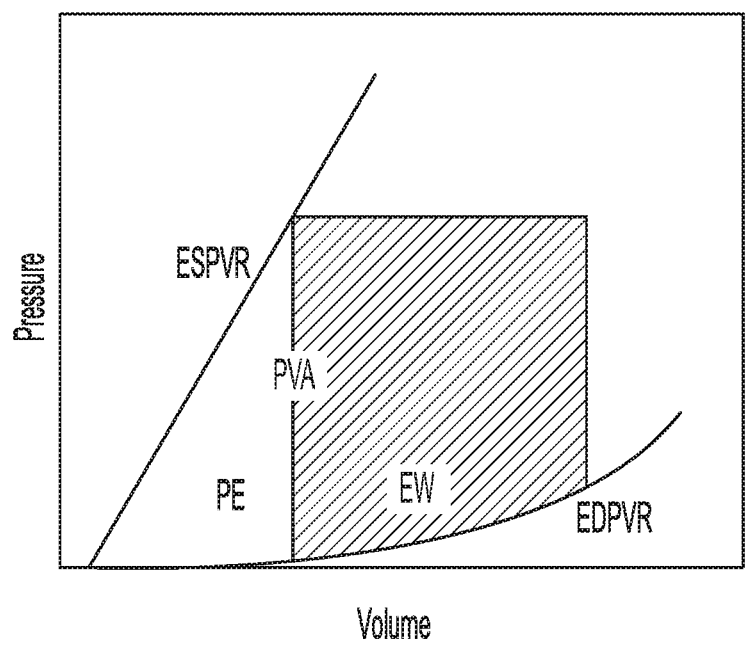
FIG. 1B illustrates an exemplary pressure-volume area (PVA) of the LV and represents the total mechanical work of the LV in a single contraction.

FIG. 1B illustrates an exemplary pressure-volume area (PVA) of the LV and represents the total mechanical work of the LV in a single contraction. PVA is a specific area circumscribed by the ESPVR and end-diastolic pressure-volume curves (EDPVR) and the systolic segment (SS) of the pressure-volume trajectory in contraction. Geometrically on the pressure-volume plane, PVA is the sum of external work (EW) and potential energy (PE), i.e., PVA=PE+EW. As illustrated in FIG. 1A, the PVA of a cardiac cycle and thus ventricular total mechanical work can be reduced by reducing the LV end systolic pressure (LVSP). For example, reducing LVSP from LVSP 112 to LVSP 122 reduces PVA (e.g., PVA 115 to PVA 125). As discussed herein, a heart pump can be used to reduce LVSP by reducing the LV volume.

Figure 2:
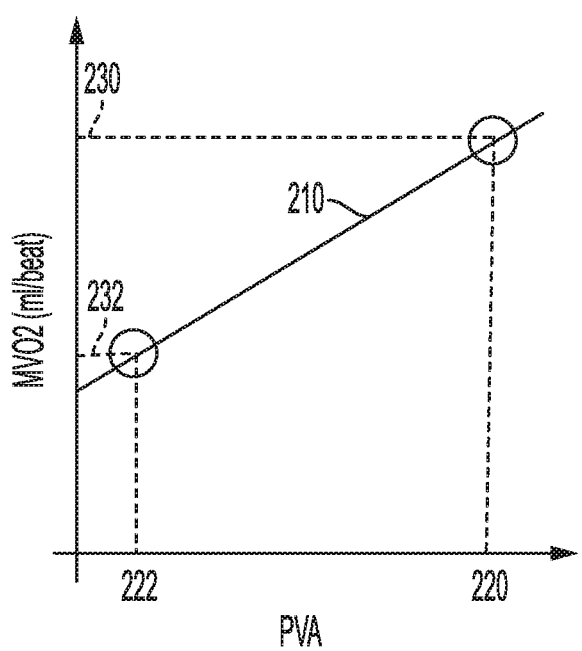
FIG. 2 illustrates the linear relationship between PVA and MVO$_2$ in a single contraction (e.g., per beat).

FIG. 2 illustrates the linear relationship between PVA and $MVO_2$ in a single contraction (e.g., per beat). It has been well established that PVA linearly correlates with $MVO_2$ (line 210). Accordingly, a reduction in PVA (e.g., PVA 220 to PVA 222) reduces $MVO_2$ (e.g., $MVO_2$ 230 to $MVO_2$ 232). It has been observed that a reduction in $MVO_2$ can reduce infarct size, or the area of dead tissue caused by a heart attack.

FIGS. 3A-3F illustrate the effect of LV mechanical unloading by a heart pump on hemodynamics, pressure-volume loops, PVA and LVSP. For example, FIGS. 3A, 3B, and 3C illustrate exemplary changes in LV pressures (LVP) and aortic pressure (AP) in time series for different levels of mechanical unloading of the LV. FIG. 3D illustrates exemplary pressure-volume loops $L_0$ (no mechanical unloading), $L_P$ (partial mechanical unloading), and $L_{MAX}$ (maximum mechanical unloading) corresponding to the respective changes in LVP. FIG. 3A illustrates exemplary LV pressure (LVP) and aortic pressure (AP) with no mechanical unloading by a heart pump. As shown in FIG. 3B, partial mechanical unloading can reduce aortic pulse pressure, but as evidenced by the pressure-volume loop Lp in FIG. 3D, the LV remains ejecting. When mechanical unloading becomes maximum, the LV no longer ejects, as shown by the pressure-volume loop L max in FIG. 3D, and the LV pressure LVP is lower than aortic pressure AP, as shown in FIG. 3C. FIG. 3E shows that maximum unloading can make PVA ($PVA_{MAX}$) and thus $MVO_2$ very small. In AMI, the maximum unloading is the condition where infarct size becomes minimum. However, mechanical unloading can almost suddenly and sharply drop LVSP even under relatively stable hemodynamic conditions as shown in the normal and AMI canine models for $LVSP_0$ and $LVSP_{AMI}$ in FIG. 3F. In AMI conditions, keeping the maximum unloading by manually controlling a heart pump can be impractical if not impossible because cardiac and hemodynamic conditions can be extremely dynamic and can change drastically. Thus, embodiments are disclosed herein of a closed feedback control system for a heart pump that can be configured to keep a predetermined target LVSP during mechanical unloading in the presence of hemodynamic instability inherent to AMI conditions.

Figure 4A:
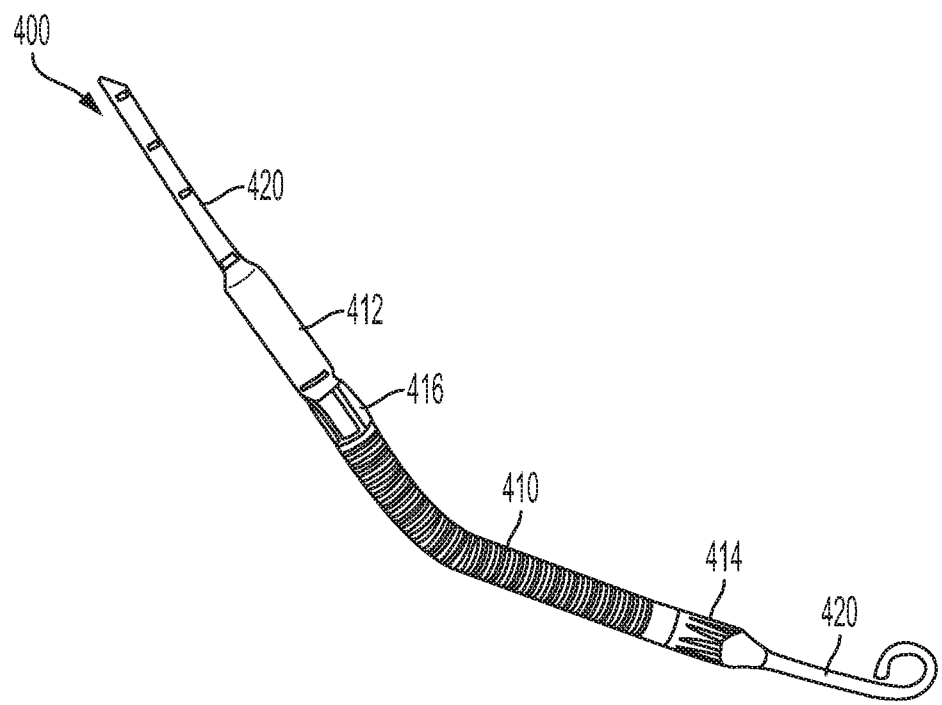
FIGS. 4A and 4B are schematic illustrations of an exemplary embodiment of a heart pump suitable for mechanical unloading of the LV.
Figure 4B:
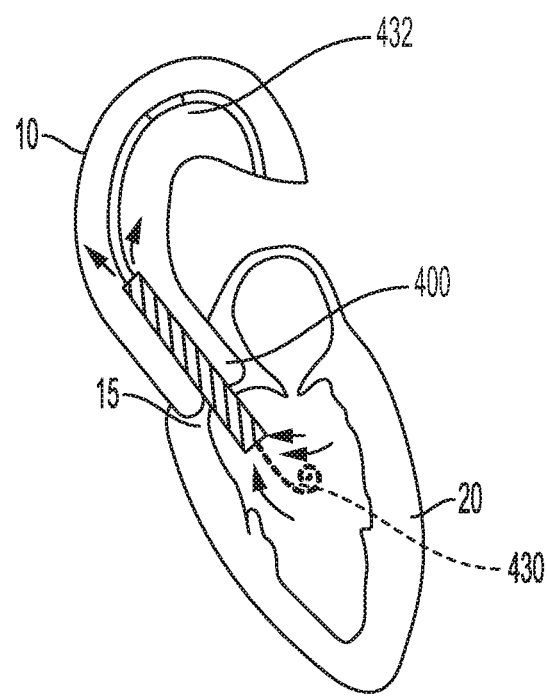

FIGS. 4A and 4B are schematic illustrations of an exemplary embodiment of a heart pump 400 suitable for mechanical unloading of the LV. In the illustrated embodiment, the heart pump 400 can include an impeller pump 410, a pump motor 412, a blood inlet 414, and a blood outlet 416. In some embodiments, the pump 400 can be disposed in a catheter 420, such that the heart pump 400 can be inserted via a standard catheterization procedure. For example, the heart pump 400 can be inserted through the femoral artery, into the ascending aorta 10, across the aortic valve 15 and into the left ventricle 20. A pressure sensor 430 can be disposed within the catheter 420 to measure LVSP during operation of the pump. In some embodiments, another pressure sensor 432 can be disposed within the catheter 420 to measure the aortic pressure. In some embodiments, the pressure sensor 432 used to measure aortic pressure and/or differential pressure can be used to calculate LVSP during operation of the pump in the absence of a pressure sensor 430 in the left ventricle. The catheter 420 can also serve as a conduit to facilitate wired connections from a remote controller or console (e.g., pump controller 510 of FIG. 5) to the pump motor 412 and on or both of the pressure sensors 430, 432.

As shown, the pump 400 can pull blood from the LV 20 into the impeller pump 410 through the blood inlet 414 and expel the blood into the ascending aorta 10 through the blood outlet 416. The flow rate of the heart pump 400 can be controlled based on the speed of the pump motor 412. As discussed in more detail below, the speed of the pump motor 412 can be controlled based on the measurements obtained from the LVSP sensor 430 and optionally aortic pressure sensor 432. In some embodiments, the heart pump 400 can pump up to 5.0 liters per minute of blood from the LV to the aorta. In some embodiments, the heart pump 400 can pump at a flow rate of more or less than 5.0 liters per minute. Examples of a heart pump suitable for use with the various embodiments can include the family of Impella® heart pumps from Abiomed, Inc. having headquarters in Danvers, Mass., including but not limited to Impella 5.0®, Impella LD®, Impella CP®, and Impella 2.5®. One of ordinary skill will readily appreciate that other left ventricular assist devices or heart pumps can be used.

Although various heart pumps are capable of unloading the LV, a pump that can generate cardiac output sufficient to support (i.e., perfuse) the whole body of patients with AMI can be useful. This is because in order to minimize PVA, the LV needs to stop ejecting regularly. This condition can be achieved when a heart pump for mechanical unloading generates flow to perfuse the whole body. Once the LV stops ejecting regularly, PVA and thus $MVO_2$ can be minimized by controlling the heart pump flow. Various embodiments of the heart pump control system disclosed herein can be used with heart pumps capable of generating cardiac output to support the whole body.

Figure 5:
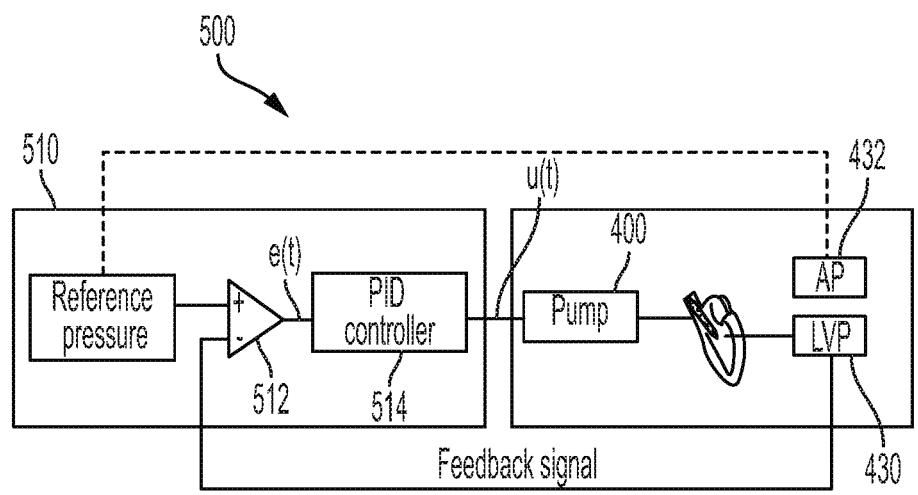
FIG. 5 is a schematic illustration of one exemplary embodiment of a closed feedback heart pump control system for controlling a heart pump to maximize mechanical unloading of the LV regardless of the presence of cardiovascular instability.

FIG. 5 is a schematic illustration of one exemplary embodiment of a closed feedback heart pump control system 4500 for controlling a heart pump to maximize mechanical unloading of the left ventricle regardless of the presence of cardiovascular instability. In the illustrated embodiment, the system 500 can include a heart pump 400, a pump controller 510, an LVSP pressure sensor 430 and, optionally, an aortic pressure sensor 432. As discussed above with respect to FIG. 4B, the heart pump 400 can be disposed within the heart to mechanically unload blood from the left ventricle into the aorta.

The pump controller 510 can be configured to control the flow rate of the pump 410 by adjusting the speed of the pump motor 412 (e.g., rotations per minute, or RPM). The pump controller 510 can transmit a command or signal over a wired or wireless connection to adjust the speed of the pump motor 412 so that the pump 410 mechanically unloads the left ventricle at a target flow rate (e.g., liters per minute) set by a target pressure.

In some embodiments, the pressure sensor(s) 430 and/or 432 can be configured to generate an output used by the pump controller 510 to measure or calculate an LVSP within the LV of the heart. For example, in some embodiments, the pressure sensor 430 can be configured to measure and output LSVP as a feedback signal to the pump controller 510. The pump controller 510 can use the LVSP as feedback information to make speed adjustments to the pump motor 412 so that the pump's flow rate can maintain LVSP at or close to a target reference pressure that is less than a normal LVSP thereby much lower than mean aortic pressure. In some embodiments, the target reference pressure can be set by manual input to the pump controller 510. In some embodiments, the target reference pressure can be set to a calculated value obtained or determined by the pump controller 510.

In order to automatically control a heart pump to minimize PVA and thereby $MVO_2$, the pump controller 510, sometimes referred to herein as a feedback controller, can be configured to control the speed, flow rate, or other operating characteristic of the heart pump to keep the LVSP at a low reference pressure level irrespective of major changes in cardiac or hemodynamic conditions. This can be achieved when the open-loop gain of the feedback controller is large enough to stabilize LVSP fluctuations resulting from AMI related major cardiac and hemodynamic instability. In some embodiments, the feedback controller of heart pump is stable with no oscillation (or effectively no oscillation) in the presence of major cardiac and hemodynamic instability. Control theory indicates that the higher the open-loop gain, the lower the stability of closed-loop feedback system. Therefore, in some embodiments, the pump controller 510 can be configured to balance open-loop gain with system stability.

In order to develop a high open-loop gain feedback controller without compromising stability, an open-loop transfer function can be determined for the plant to be controlled. The plant can represent the heart augmented with the heart pump. For example, in some embodiments, the plant can model dynamic changes in LVSP in response to changes in pump speed of a heart pump used for mechanical unloading. For example, the plant can be defined as a single-input single-output (SISO) system where the input is a pump speed controlling command (e.g., rpm) and the output is LVSP (e.g., mmHg). In cardiovascular physiology, the transfer function of how changes in the pump speed dynamically affect the LVSP has never been studied. In some embodiments, the transfer function of the plant can be defined using other inputs, such as flow rate (e.g., milliliters per second) or other operating characteristic of the heart pump. In some embodiments, the transfer function of the plant can be defined using other outputs, such as LV diastolic pressure, aortic pressure or other property of the cardiovascular system (e.g., heart) that can be measured or estimated using a sensor (e.g., sensors 430, 432).

In some embodiments, computational modeling of cardiovascular system can be employed to estimate an approximated transfer function from the pump speed to LVSP. In some embodiments, the transfer function can be approximated and reduced to a second order system with a delay as:

$$H(f) = \frac{K}{1 + 2\zeta \frac{f}{f_N} j + \left(\frac{f}{f_N} j\right)^2} \exp(-2\pi f L j)$$

where the four parameters are the gain K, damping factor $\zeta$, natural frequency $f_N$ and delay time L. The term j represents the imaginary unit, where $j^2=-1$. Since the second order transfer function H(f) results from the basic anatomy of the cardiovascular system, the transfer function can apply to many species having a similar anatomy to the human cardiovascular system. The transfer function H(f) can also be used as the plant for modeling the heart augmented with the heart pump under disease states, because such conditions are unlikely to involve major anatomical changes of the cardiovascular system.

In some embodiments, the four parameters of the plant transfer function H(f) can include a gain K that is equal to or about 0.013 mmHg/rpm, a damping factor $\zeta$ that is equal to or about 1.9, a natural frequency $f_N$ that is equal to or about 0.41 Hz and a delay time L that is equal to or about 0.03 seconds. As discussed with respect to FIG. 9 below, in some embodiments, the values of one or more of the parameters of the plant transfer function H(f) can be changed in response to changes in AMI and volume loading conditions. Although the approximate values of the foregoing parameters are based on animal experiments and canine models under AMI conditions, one of ordinary skill in the art will recognize that these parameters can be adjusted to accommodate any variation associated with the human cardiovascular system.

On the basis of the identified plant transfer function H(f), the pump controller 510 can be configured to keep LVSP at a constant value irrespective of changes in cardiac and hemodynamic condition. For example, as shown in FIG. 5, in some embodiments, the pump controller 510 can include a comparator 512 and a proportional-integral (PI) controller or a proportional-integral-derivative (PID) controller 514. The comparator 512 can be coupled to the pressure sensor 430 and configured to receive a measurement of LSVP output from the pressure sensor. The comparator 512 can be configured to compare the target reference pressure to LVSP measured within the left ventricle and output a pressure difference or error signal e(t) to the PID controller 514.

The PID controller can be configured to implement the following equation:

$$u(t) = K_p e(t) + K_i \int_0^t e(\tau) d\tau + K_d \frac{de(t)}{dt}$$

where $K_p$ is the proportional gain, $K_i$ is the integral gain, and $K_d$ is the derivative gain, t is the time or instantaneous time, and $\tau$ is the variable of integration that takes on values from time 0 to present time t. The integral term can be configured to make the dc gain infinity of the controller effectively equal to infinity. The equation u(t) can be rewritten in the Laplace domain as $U(s)=K_p+K_i/s$ and $K_d s$.

The values of $K_p$, $K_i$, and $K_d$ can be selected to tune the system 500, such that the time or frequency response of LVSP of the closed-loop system can be optimized with respect to a step change in pump speed or a corresponding flow rate. For example, in some embodiments, the values of $K_p$, $K_i$, and $K_d$ can be selected such that a measured LVSP can reach a target reference pressure with minimal overshoot and time delay in response to a corresponding adjustment in pump speed. For example, in some embodiments, (i) the overshoot of the step response of LVSP under the closed loop condition can be less than about 10%, (ii) the time to reach the steady state response of LVSP can be shorter than a predetermined clinically relevant response time (e.g., about 60 seconds), and/or (iii) the steady state deviation from the target pressure can average zero. In some embodiments, the PID controller 514 can be implemented so that the feedback control system 500 is stable and can satisfy one or more of such constraints in the presence of a change in the open loop gain of the plant, e.g., up to or more than 16 times.

In some embodiments, based on the identified transfer function of the plant H(f), the minimum realization of the controller can be a proportional-integral (PI) controller with a proportional gain $K_p$ that is equal to or about 40, an integral gain $K_i$ that is equal to or about 20 and a derivative gain $K_d$ that is equal to or about 0. The combination of these values for gains $K_p$ and $K_i$ can allow the system to maintain LVSP at a constant value in the presence of AMI-induced major instability of cardiac and hemodynamic conditions including a change in the open-loop gain of the plant, e.g., up to or more than a factor equal to or about 16. In some embodiments, one or more of the respective gain parameters $K_p$, $K_i$ and $K_d$ can be adjusted in response to changes in design requirements and/or open loop gain of the plant.

Figure 6:
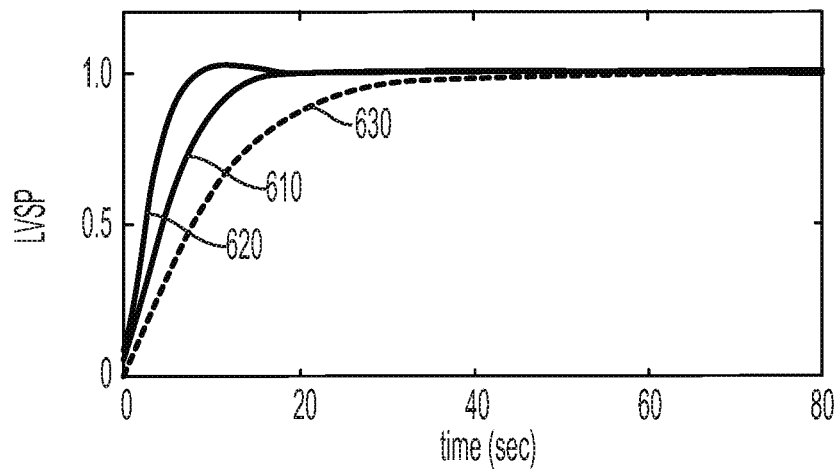
FIG. 6 illustrates exemplary step responses of LVSP under the control of the feedback heart pump control system of FIG. 5.

FIG. 6 illustrates exemplary step responses of LVSP under the control of the closed-feedback heart pump control system 500 of FIG. 5 using the controller parameters described above. For example, as shown, the control system 500 can provide a step response 610 for LVSP that exhibits no overshoot and reaches steady state in approximately 20 seconds under the AMI condition. When the plant exhibits an open loop gain that is 4 times greater than normal, the control system 500 can provide a step response 620 for LVSP that exhibits an overshoot of less than about 5% and reaches the steady state in approximately less than about 20 seconds. When the plant exhibits an open loop gain that is one quarter (¼) times less than normal, the control system can provide a step response 630 for LVSP that exhibits no overshoot and reaches steady state in about 40 seconds.

Based on numerous animal experiments, which were exhaustively conducted under extreme AMI conditions, the open loop gains of the plant were observed to vary within a range between a factor of 4 to ¼. In clinical applications, the open loop gain associated with human patients should change no more than a factor of 16. A step response that takes between about 20 seconds and about 40 seconds to reach steady state should be sufficient to avoid adversary effects in the outcome relating to ventricular unloading therapy. However, one skilled in the art will recognize that the control system can be configured to reach steady state in other clinically relevant response times.

Figure 7A:
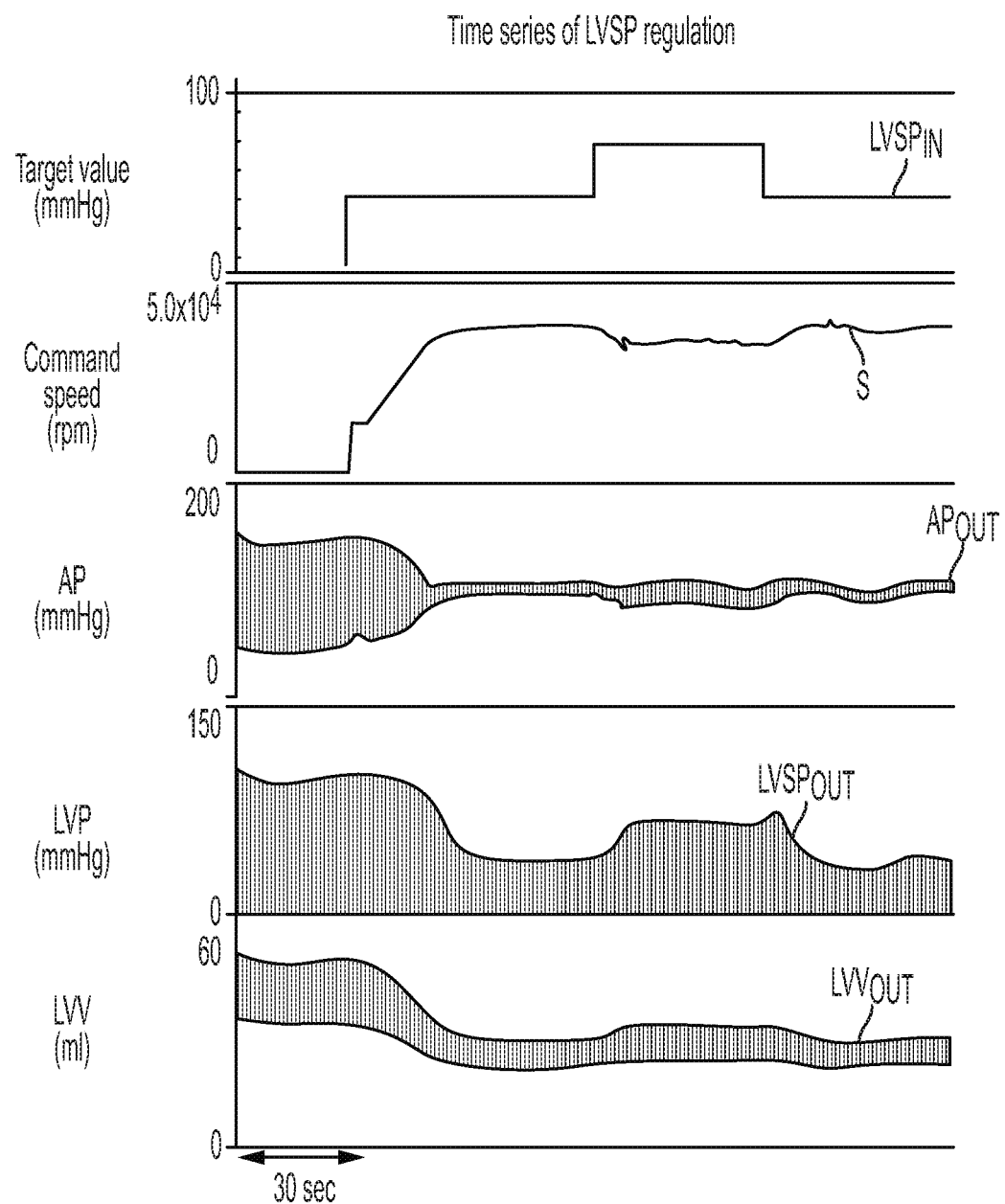
FIG. 7A illustrates exemplary performance of the feedback heart pump control system of FIG. 5 in response to changes in target reference pressure values.
Figure 7B:
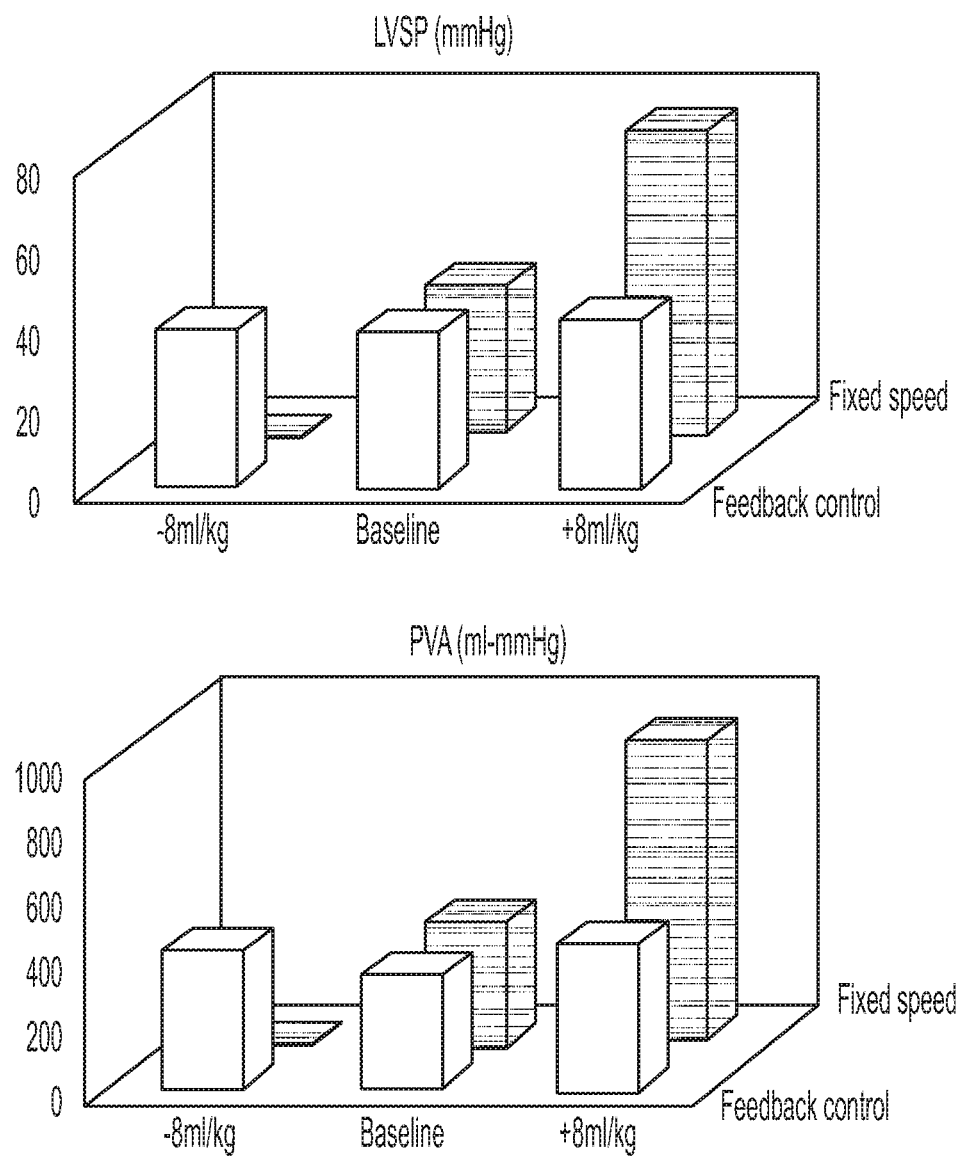
FIG. 7B illustrates exemplary performance of the feedback heart pump control system of FIG. 5 in the stabilization of relevant metrics representing MVO$_2$ consumption in the presence of major LV volume perturbations.

FIGS. 7A and 7B illustrate exemplary performance of the closed feedback heart pump control system of FIG. 5 using pump speed to control LVSP. For example, FIG. 7A illustrates that as the input target reference pressure $LVSP_{IN}$ is changed stepwise from 40, 70 and 40 mmHg, the control system 500 can adjust the commanded pump speed S to provide an output $LVSP_{OUT}$ that follows the target pressures. FIG. 7A also shows changes in output aortic pressure $AP_{OUT}$ and LV volume $LVV_{OUT}$ associated with controlled output LVSP.

FIG. 7B shows the stabilization of relevant metrics representing $MVO_2$ consumption (e.g., LVSP and PVA) of the LV in the presence of major volume perturbation (e.g., an increase or decrease in left ventricular volume). Volume perturbation is a hemodynamic instability inherent to AMI. As shown in FIG. 7B, despite the major changes in volume (e.g., ±8 ml/kg), LVSP and PVA can remain substantially constant by controlling the pump speed of a heart pump (e.g., 400) using the embodiment feedback control system 500 to maintain the target LVSP. In comparison, LVSP and PVA can vary significantly in response to major volume perturbation of the LV using a heart pump at fixed speeds.

In some embodiments, where a quicker response or a more stable response is needed depending upon the purpose, one of ordinary skill in the art will recognize that one or more of the gain parameters Kp, Ki and Kd of the PID controller 514 can be adjusted. Therefore, although specific gain parameter values are disclosed herein for the PID controller, such values are exemplary and not intended to be limiting.

As discussed above, the embodiment heart pump control system 500 can be configured to maintain LVSP at a target reference pressure determined to minimize $MVO_2$ of the LV. For example, as shown in FIGS. 1 and 2, $MVO_2$ can be minimized by minimizing the PVA of the LV. In theory, a PVA of zero can make $MVO_2$ minimum. However, maintaining PVA at zero, which means that LVSP is zero mmHg, is very difficult to safely and stably achieve because even a minor reduction of LVSP below zero can result in the pump creating major suction within the LV that can damage the heart. Therefore, in some embodiments, the closed feedback heart pump control system 500 of FIG. 5 can be configured to maintain LVSP at a target LVSP that provides an approximately minimum $MVO_2$ and is still safely and stably controllable by the feedback system. For example, in some embodiments, the target LVSP can be determined based on the relationship between fractional LVSP and recruited fractional PVA as shown in FIGS. 8A and 8B.

Figure 8A:
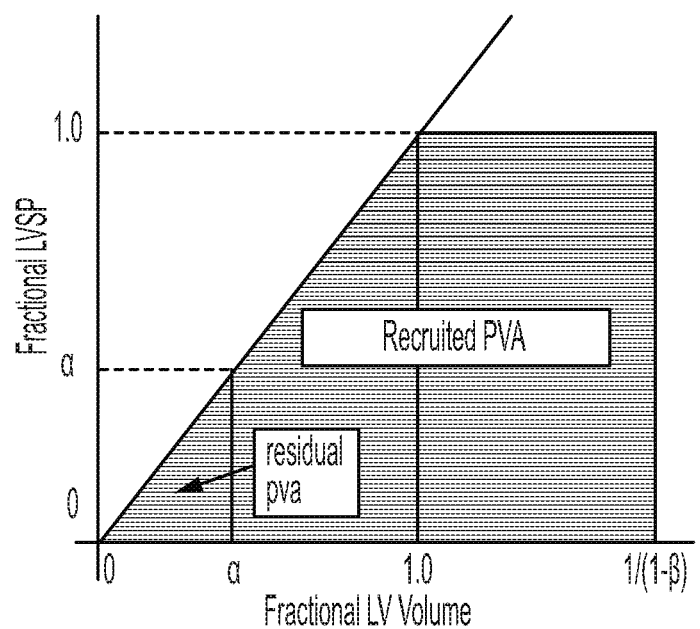
FIGS. 8A and 8B illustrates the relationship between the PVA recruitment fraction and the fractional LVSP to determine a target reference pressure.

FIG. 8A illustrates the relationship between the fractional LVSP and fractional LV volume. As shown, the pressure and volume are normalized to unity at end-systole in normal ejecting contraction. Fractional LVSP "a" is the ratio of LVSP during unloading to end-systolic pressure in normal ejection defining the operating condition of LV unloading. The lower fractional LVSP α, the stronger unloading. For a given fractional LVSP α, fractional LV volume becomes also a because LV volume is normalized by end-systolic volume. LV end-diastolic volume is given by 1/(1−β) where β is LV ejection fraction, i.e., stroke volume divided by end-diastolic volume.

Recruited PVA is the PVA recruited by LV unloading at the operating condition of a. Residual PVA is PVA that remains by unloading at the operating condition of a. Fractional PVA recruitment is defined by the ratio of residual PVA to the sum of recruited PVA and residual PVA indicating what percentage of total PVA is recruited by LV unloading. Mechanical unloading reduces fractional LVSP α, increases the recruited PVA and results in a reduction of residual PVA of the LV.

Figure 8B:
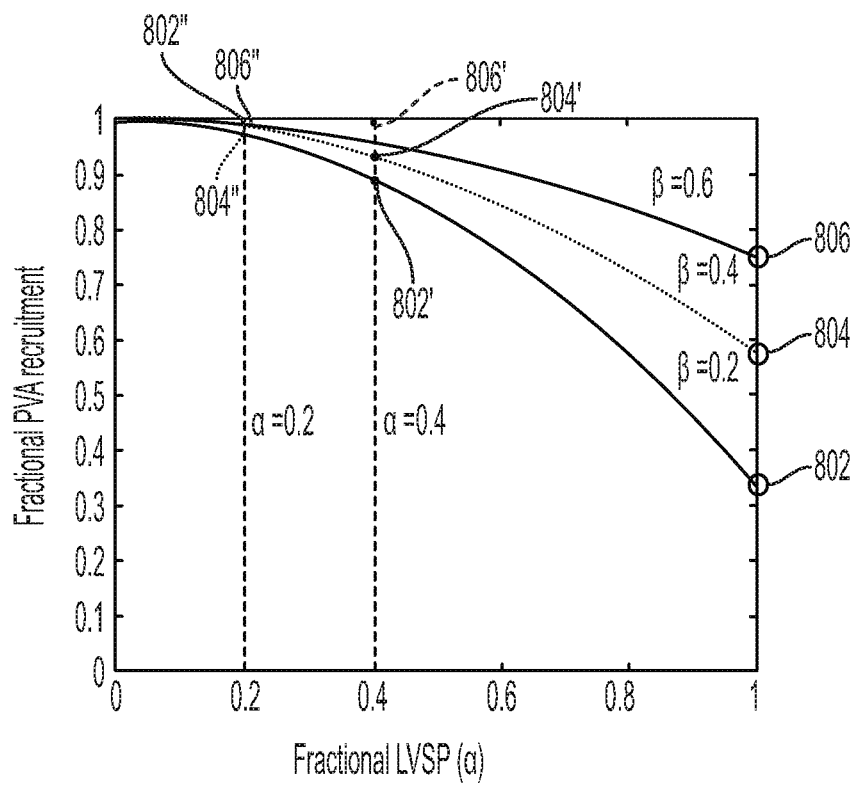

FIG. 8B illustrates the fractional PVA recruitment as a function of fractional LVSP "α" under various ejection fractions "β." As shown, the fractional PVA recruitment decreases with fractional LVSP α. For example, at α=1 (i.e., where fractional LV volume=1), the fractional PVA recruitments 806, 804, and 802 are equal to 0.75, 0.57 and 0.33 for ejection fractions β of 0.6, 0.4 and 0.2, respectively. This means that a poorly contracting LV can require larger unloading to reduce PVA. For α=0.4, the fractional PVA recruitments 806', 804', 802', can be greater than or equal to 0.9 regardless of the ejection fraction β. For α=0.2, the fractional PVA recruitments 806", 804", 802" can be greater than or equal to 0.97 regardless of the ejection fraction 3.

Therefore, in some embodiments, the target LVSP can be set equal to the product of the end-systolic pressure in a normal ejecting beat and the fractional LVSP α, where α is a value between about 0.2 and about 0.4, to minimize the PVA of the LV by about 90% to 97%. The end-systolic pressure during a normal ejecting beat is typically between 70 and 110 mmHg. A target LVSP within such a range can be safely and stably achievable through mechanical unloading with a heart pump under the control of the embodiment feedback system 500 of FIG. 5. A reduction of PVA by about 90% to 97% can be translated into a corresponding reduction of $MVO_2$ about 45% to 48.5%, respectively, assuming 50% of $MVO_2$ is PVA independent. In the presence of significant noise in evaluating infarct size, the minor difference of $MVO_2$ is unlikely to affect infarct size. Such a reduction of $MVO_2$ can achieve a major oxygen sparing and thereby reduce infarct size and subsequent heart failure.

In some embodiments, the target LVSP can be set equal to the product of the mean aortic pressure and the fractional LVSP α, where a is a value between about 0.2 and about 0.4, to minimize the PVA of the LV by about 90% to about 97%. As discussed above, a reduction of PVA by about 90% to 97% can correspond to a reduction of $MVO_2$ by about 45 to about 48.5%, assuming about 50% of $MVO_2$ is PVA independent. Such a reduction of $MVO_2$ can achieve a major oxygen sparing and thereby reduce infarct size and subsequent heart failure.

In some embodiments, where the hemodynamics of AMI patients are relatively stable, including aortic pressure, the target reference pressure (e.g., target LSVP) can be set to a fixed fraction of mean aortic pressure, such as but not limited to the fraction is between about 0.2 and about 0.4. In some embodiments, the target reference pressure can be set to a fixed fraction of other hemodynamic parameter that can be measured or estimated. Once the target pressure is set, it will not be changed until clinical necessity emerges. This simplifies to set the target pressure dependent upon the patients hemodynamic condition.

Figure 9:
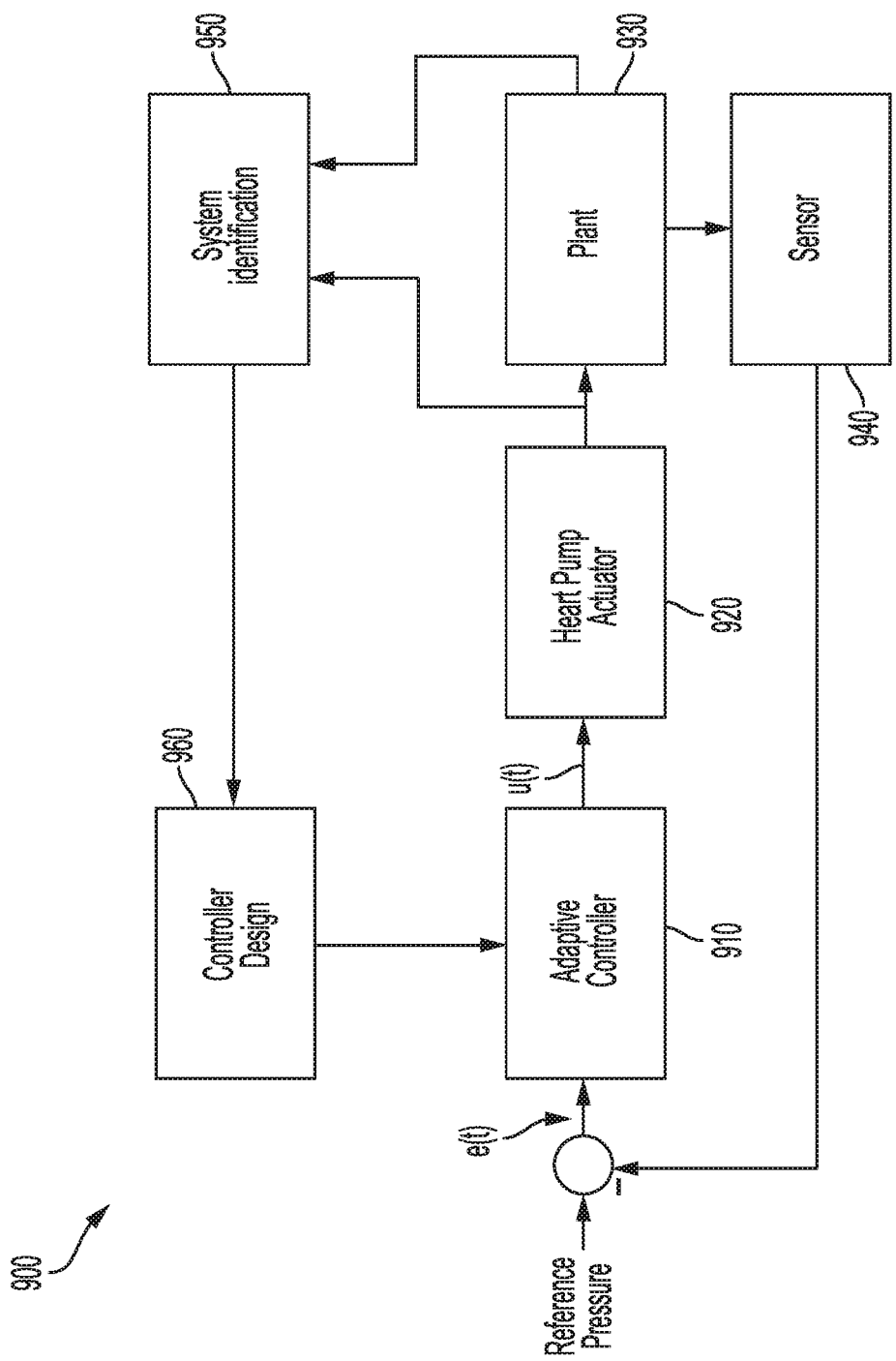
FIG. 9 is a schematic illustration of one exemplary embodiment of an adaptive feedback heart pump control system.

FIG. 9 is a schematic illustration of one exemplary embodiment of an adaptive feedback heart pump control system 900. As shown, the control system 900 can include a comparator 905, an adaptive pump controller 910, a heart pump actuator 920, a plant model 930, one or more sensors 940, a system identification module 950, and a controller design module 960. Except as described below or as will be readily appreciated by one having ordinary skill in the art, the control system 900 can be substantially similar to the control system 500 described above with respect to FIGS. 4 and 5. A detailed description of the structure and function thereof is thus omitted here for the sake of brevity. The control system 900 can include any one or more of the features of the control system 500 described above.

In some embodiments, the adaptive feedback heart pump control system 900 can be used to control a heart pump to maintain a target LVSP or AP in AMI patients that may require more complex applications of mechanical unloading. For example, more complex application of mechanical unloading may be expected in patients with right ventricular failure, life-threatening arrhythmias and with other mechanical circulatory device. Accordingly, a feedback heart pump control system that is configured to control the plant associated with a fixed transfer function may not guarantee to keep LVSP and PVA constant. Thus, the system identification module 950 and the controller design module 960 can be used to adaptively configure the control system 900 to control the heart pump 920 based on a continuous and/or periodic identification and updating of the plant model 930 that represents the heart augmented with a heart pump (e.g., 400). By this way, the adaptive pump controller 910 can be adaptively configured to minimize PVA and MOV2 in patients with AMI under a wide variety of pathological states.

In some embodiments, the system identification module 950 can be configured to periodically or continuously monitor and update the plant transfer function, and the controller design module 960 can be configured to update one or more parameters of the adaptive pump controller 910 in response to determined changes in the plant transfer function. For example, in some embodiments, the system identification module 950 can be configured to adjust one or more of the parameters of the second order transfer function H(f) of the plant, such as the gain K, damping factor ζ, natural frequency $f_N$ and/or delay time L, in response to changes in the correlation between pump speed and LVSP. In some embodiments, the system identification module 940 can be configured to model the plant using a transfer function other than the second order transfer function H(f). In some embodiments, the system identification module 950 can be configured to change the plant transfer function based on sensor measurement of LVSP in response to changes in pump speed.

Based on the determined changes in the plant transfer function, the controller design module 960 can adjust one or more parameters of the adaptive pump controller 910. For example, where the adaptive pump controller is a PI or PID controller, the controller design module 960 can adjust one or more of a proportional gain $K_p$, an integral gain $K_i$ and a derivative gain $K_d$ associated with the controller. The adjusted values of $K_p$, $K_i$, and $K_d$ can be selected such that a measured LVSP can reach a target reference pressure with minimal overshoot and time delay in response to a corresponding adjustment in pump speed.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the claims.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver smart objects, e.g., a combination of a DSP and a microprocessor, two or more microprocessors, one or more microprocessors in conjunction with a DSP core, or any other such configuration. Alternatively, some operations or methods may be performed by circuitry that is specific to a given function.

In one or more aspects, the functions described may be implemented in hardware, software, firmware, or any combination thereof. If implemented in software, the functions may be stored as one or more instructions or code on a non-transitory computer-readable storage medium or non-transitory processor-readable storage medium. The operations of a method or algorithm disclosed herein may be embodied in a processor-executable software module or processor-executable instructions, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage smart objects, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

The invention claimed is:

1. A system for cardiac support, the system comprising:
a heart pump comprising
  a first portion configured to be positioned within a patient's heart;
  a first sensor positioned within the first portion of the heart pump and configured to generate an output used to measure or calculate a left ventricular systolic pressure (LVSP) within a left ventricle of the patient; and
a controller coupled to the heart pump and configured to measure or calculate the LVSP based on the output of the first sensor and to control an operation of the heart pump to mechanically unload the left ventricle based on the measured or calculated LVSP,
wherein the heart pump has a pump speed and a flow rate, and the controller is configured to control one or more of the pump speed and the flow rate of the heart pump, such that the LVSP within the left ventricle is maintained at a target reference pressure, and
wherein the controller is configured to set the target reference pressure to a fraction of an end-systolic pressure in a normal ejecting beat, wherein the end-systolic pressure is measured by the first sensor, and wherein the fraction is between about 0.2 and about 0.4.

2. A system for cardiac support, the system comprising:
a heart pump comprising
  a first portion configured to be positioned within a patient's heart;
  a first sensor positioned within the first portion of the heart pump and configured to generate an output used to measure or calculate a left ventricular systolic pressure (LVSP) within a left ventricle of the patient; and
a controller coupled to the heart pump and configured to measure or calculate the LVSP based on the output of the first sensor and to control an operation of the heart pump to mechanically unload the left ventricle based on the measured or calculated LVSP,
wherein the heart pump has a pump speed and a flow rate, and the controller is configured to control one or more of the pump speed and the flow rate of the heart pump such that the LVSP within the left ventricle is maintained at a target reference pressure, and
wherein the system further comprises a second sensor positioned within a second portion of the heart pump and configured to generate an output used to measure or calculate a mean aortic pressure, and wherein the controller is configured to set the target reference pressure to a fraction of the mean aortic pressure, wherein the fraction is between about 0.2 and about 0.4.

3. A system for cardiac support, the system comprising:
a heart pump comprising
  a first portion configured to be positioned within a patient's heart;
  a first sensor positioned within the first portion of the heart pump and configured to generate an output used to measure or calculate a left ventricular systolic pressure (LVSP) within a left ventricle of the patient; and
a controller coupled to the heart pump and configured to measure or calculate the LVSP based on the output of the first sensor and to control an operation of the heart pump to mechanically unload the left ventricle based on the measured or calculated LVSP,
wherein the heart pump has a pump speed and a flow rate, and the controller is configured to control one or more of the pump speed and the flow rate of the heart pump, such that the LVSP within the left ventricle is maintained at a target reference pressure, and
wherein the controller is configured to set the target reference pressure to reduce a pressure-volume area (PVA) of the left ventricle, wherein the controller estimates PVA based on the measured or calculated LVSP and one or more measurements of a left ventricle volume.

4. The system of claim 3, wherein the controller is configured to set the target reference pressure to reduce the PVA of the left ventricle by about 90% to about 97%.

5. The system of claim 3, wherein the controller is configured to set the target reference pressure to reduce myocardial oxygen consumption ($MVO_2$) of the left ventricle, wherein the controller estimates the $MVO_2$ based on a linear relationship between the $MVO_2$ and the PVA.

6. The system of claim 5, wherein the controller is configured to set the target reference pressure to reduce the $MVO_2$ of the left ventricle by about 45% to about 48.5%.

7. A system for cardiac support, the system comprising:
a heart pump comprising
  a first portion configured to be positioned within a patient's heart;
  a first sensor positioned within the first portion of the heart pump and configured to generate an output used to measure or calculate a left ventricular systolic pressure (LVSP) within a left ventricle of the patient; and a controller coupled to the heart pump and configured to measure or calculate the LVSP based on the output of the first sensor and to control an operation of the heart pump to mechanically unload the left ventricle based on the measured or calculated LVSP, wherein the heart pump has a pump speed and a flow rate, and the controller is configured to control one or more of the pump speed and the flow rate of the heart pump, such that the LVSP within the left ventricle is maintained at a target reference pressure, and wherein the controller is configured to control the one or more of the pump speed and the flow rate of the heart pump to maintain the LVSP at the target reference pressure based on a plant transfer function that models changes in LVSP in response to changes in the pump speed, wherein the system further comprises a non-transitory computer-readable storage medium or a non-transitory processor-readable storage medium configured to store the plant transfer function as one or more instructions or code, wherein the plant transfer function is a second order with a delay.

8. The system of claim 7, wherein the plant transfer function is the second order delay system with a time lag defined as:

$$H(f) = \frac{K}{1 + 2\zeta \frac{f}{f_N} j + \left(\frac{f}{f_N} j\right)^2} \exp(-2\pi f L j)$$

where K is a gain, $\zeta$ is a damping factor, $f_N$ is a natural frequency, and L is the time lag.

9. The system of claim 8, wherein the gain K is equal to about 0.013 mmHg/rpm, the damping factor $\zeta$ is equal to about 1.9, the natural frequency $f_N$ is equal to about 0.41 Hz and the time lag L is equal to about 0.03 seconds.

10. The system of claim 9, wherein the controller is configured to control the one or more of the pump speed and the flow rate of the heart pump such that the LVSP reaches the target reference pressure in less than a clinically predetermined response time and with an overshoot of less than 10% of the target reference pressure.

11. The system of claim 9, wherein the controller is configured to control the one or more of the pump speed and the flow rate of the heart pump to maintain the LVSP at the target reference pressure when an open loop gain of the plant transfer function changes by a factor of 16 or less.

12. The system of claim 9, wherein the controller includes a proportional-integral controller configured with a proportional gain equal to about 40, an integral gain equal to about 20, and a derivative gain equal to about 0.

13. The system of claim 9, wherein the controller includes an adaptive control mechanism configured to update the plant transfer function and reconfigure the controller to control the one or more of the pump speed and the flow rate of the heart pump in response to changes in the plant transfer function.

14. A method for treating an acute myocardial infarction (AMI) patient, comprising:

positioning a first portion of a heart pump within an AMI patient's heart;

measuring or calculating a left ventricular systolic pressure (LVSP) within a left ventricle of the AMI patient using an output generated by at least one sensor positioned within the first portion of the heart pump; and controlling an operation of the heart pump to mechanically unload the left ventricle based on the measured or calculated LVSP, wherein controlling the operation of the heart pump comprises controlling one or more of a pump speed and a flow rate of the heart pump, such that the LVSP within the left ventricle is maintained at a target reference pressure, and the method further comprising measuring or calculating end-systolic pressure in a normal ejecting beat; and setting-the target reference pressure to a fraction of the end-systolic pressure, wherein the fraction is between about 0.2 and about 0.4.

15. A method for treating an acute myocardial infarction (AMI) patient, comprising:

positioning a first portion of a heart pump within an AMI patient's heart;

measuring or calculating a left ventricular systolic pressure (LVSP) within a left ventricle of the AMI patient using an output generated by at least one sensor positioned within the first portion of the heart pump; and controlling an operation of the heart pump to mechanically unload the left ventricle based on the measured or calculated LVSP, wherein controlling the operation of the heart pump comprises controlling one or more of a pump speed and a flow rate of the heart pump, such that the LVSP within the left ventricle is maintained at a target reference pressure, and the method further comprising measuring or calculating a mean aortic pressure; and setting the target reference pressure to a fraction of the measured or calculated mean aortic pressure, wherein the fraction is between about 0.2 and about 0.4.

16. A method for treating an acute myocardial infarction (AMI) patient, comprising:

positioning a first portion of a heart pump within an AMI patient's heart;

measuring or calculating a left ventricular systolic pressure (LVSP) within a left ventricle of the AMI patient using an output generated by at least one sensor positioned within the first portion of the heart pump; and controlling an operation of the heart pump to mechanically unload the left ventricle based on the measured or calculated LVSP, wherein controlling the operation of the heart pump comprises controlling one or more of a pump speed and a flow rate of the heart pump, such that the LVSP within the left ventricle is maintained at a target reference pressure, and further comprising estimating a pressure-volume area (PVA) of the left ventricle based on the measured or calculated LVSP and one or more measurements of a left ventricle volume, and setting the target reference pressure to reduce the PVA by about 90% to about 97%.

17. The method of claim 16, further comprising estimating a myocardial oxygen consumption (MVO2) based on a linear relationship between the MVO2 and the PVA, and setting the target reference pressure to reduce myocardial oxygen consumption ($MVO_2$) of the left ventricle by about 45% to about 48.5%.

18. A system for cardiac support, the system comprising:
a heart pump comprising
a first portion configured to be positioned within a patient's heart;
a first sensor positioned within the first portion of the heart pump and configured to generate an output used to measure or calculate a left ventricular systolic pressure (LVSP) within a left ventricle of the patient; and
a controller coupled to the heart pump and configured to measure or calculate the LVSP based on the output of the first sensor and to control an operation of the heart pump to mechanically unload the left ventricle based on the measured or calculated LVSP,
wherein the heart pump has a pump speed and a flow rate, and the controller is configured to control one or more of the pump speed and the flow rate of the heart pump, such that the LVSP within the left ventricle is maintained at a target reference pressure, and
the system further comprising a storage medium configured to store a plant transfer function, wherein the controller is configured to control the heart pump to maintain the LVSP at a target reference pressure based on the plant transfer function that models changes in LVSP in response to changes in pump speed, wherein the plant transfer function is second order with a delay.

19. The system of claim 18, wherein the delay is based on a ratio between an exponential function and a second order function.

20. The system of claim 19, wherein the second order function includes a damping factor $\zeta$ that is a coefficient of a first order component of the second order function.

* * * * *

UNITED STATES PATENT AND TRADEMARK OFFICE
CERTIFICATE OF CORRECTION

PATENT NO. : 10,960,118 B2
APPLICATION NO. : 16/050542
DATED : March 30, 2021
INVENTOR(S) : Kenji Sunagawa It is certified that error appears in the above-identified patent and that said Letters Patent is hereby corrected as shown below:

On the Title Page

Column 2, item [57], Line 6:
Delete: "(MVO2)"; and insert -- (MVO$_2$) --

Column 2, item [57], Line 10:
Delete: "(LSVP)"; and insert -- LVSP --

In the Drawings

Figures Sheet 2 of 9, FIG. 2:
Delete: "MVO2"; and insert -- MVO$_2$ --

In the Specification

Column 2, Line 37:
Delete: "(LSVP)"; and insert -- LVSP --

Column 3, Line 36:
Delete: "LSVP"; and insert -- LVSP --

Column 5, Line 6:
Delete: "(ESVPR,"; and insert -- (ESPVR, --

Column 5, Line 45:
Delete: "Lp"; and insert -- L$_P$ --

Column 5, Line 48:
Delete: "L max"; and insert -- L$_{MAX}$ --

Signed and Sealed this
Twenty-eighth Day of June, 2022

*Katherine Kelly Vidal*
Katherine Kelly Vidal
*Director of the United States Patent and Trademark Office*

CERTIFICATE OF CORRECTION (continued)
U.S. Pat. No. 10,960,118 B2

Column 6, Line 54:
Delete: "4500"; and insert -- 500 --

Column 7, Line 9:
Delete: "LSVP"; and insert -- LVSP --

Column 8, Line 35:
Delete: "LSVP"; and insert -- LVSP --

Column 10, Line 6:
Delete: "Kp, Ki and Kd"; and insert -- $K_p$, $K_i$ and $K_d$ --

Column 10, Line 32:
Delete: ""a""; and insert -- "α" --

Column 10, Line 42:
Delete: "a."; and insert -- α. --

Column 10, Line 43:
Delete: "a."; and insert -- α. --

Column 10, Line 62:
Delete: "3."; and insert -- β. --

Column 11, Line 15:
Delete: "a"; and insert -- α --

Column 11, Line 25:
Delete: "LSVP)"; and insert -- LVSP) --

Column 11, Line 65:
Delete: "MOV2"; and insert -- $MVO_2$ --

Column 12, Line 13:
Delete: "940"; and insert -- 950 --

In the Claims

Column 13, Claim 1, Line 45:
Delete: "comprising"; and insert -- comprising: --

Column 14, Claim 2, Line 2:
Delete: "comprising"; and insert -- comprising: --

Column 14, Claim 2, Line 17:
Delete: "pump"; and insert -- pump, --

CERTIFICATE OF CORRECTION (continued)
U.S. Pat. No. 10,960,118 B2

Column 14, Claim 3, Line 28:
Delete: "comprising"; and insert -- comprising: --

Column 14, Claim 7, Line 63:
Delete: "comprising"; and insert -- comprising: --

Column 16, Claim 14, Line 11:
Delete: "comprising"; and insert -- comprising: --

Column 16, Claim 15, Line 35:
Delete: "comprising"; and insert -- comprising: --

Column 16, Claim 16, Line 57:
Delete: "comprising"; and insert -- comprising: --

Column 16, Claim 17, Line 64:
Delete: "comprising"; and insert -- comprising: --

Column 16, Claim 17, Line 65:
Delete: "(MVO2)"; and insert -- $(MVO_2)$ --

Column 16, Claim 17, Line 66:
Delete: "(MVO2)"; and insert -- $(MVO_2)$ --

Column 17, Claim 18, Line 5:
Delete: "comprising"; and insert -- comprising: --